United States Patent [19]

Draper, Jr.

[11] 4,219,018
[45] Aug. 26, 1980

[54] EARPLUG UNIT WITH INSERTER AND TIE

[75] Inventor: Weston E. Draper, Jr., Diamond Bar, Calif.

[73] Assignee: Norton Company, Worcester, Mass.

[21] Appl. No.: 24,956

[22] Filed: Mar. 29, 1979

[51] Int. Cl.³ .............................................. A61F 11/02
[52] U.S. Cl. ................................................. 128/152
[58] Field of Search .................... 128/152, 151, 140 N, 128/263

[56] References Cited

U.S. PATENT DOCUMENTS

| D. 195,322 | 5/1963 | Hill | 128/152 X |
| D. 241,881 | 10/1976 | Peterson et al. | 128/152 X |
| 679,925 | 8/1901 | Vickers | 128/152 |
| 2,094,534 | 9/1937 | Halle | 128/152 |
| 2,230,738 | 2/1941 | Baum | 128/152 |
| 2,393,340 | 1/1946 | Russell | 128/152 |
| 3,259,128 | 7/1966 | Leight | 128/152 |
| 3,301,253 | 1/1967 | Glorig | 128/152 |
| 3,415,246 | 12/1968 | Hill | 128/152 |
| 3,871,372 | 3/1975 | Bivins | 128/152 |
| 3,915,166 | 10/1975 | McCrink | 128/152 |

FOREIGN PATENT DOCUMENTS 56662 7/1890 Fed. Rep. of Germany ........... 128/152

OTHER PUBLICATIONS

Norton Safety Products Catalog No. 3-200, Nov. 1976, "Norton Com-Fit Earplugs".

Primary Examiner—Henry J. Recla
Attorney, Agent, or Firm—Walter Fred

[57] ABSTRACT

Earplug unit with inserter and tie adapted to be worn as a unit which can be folded and compacted into a relatively small carrying case, comprises one or a pair of earplugs (10) (30) each having an outer end attached to one or both ends of a tie member (22) (32) on which is slideably carried and retained an earplug inserter moveable from a carrying position into engagement with the outer end of an earplug for its insertion into the auditory canal (c) of an ear (E).

7 Claims, 2 Drawing Figures

EARPLUG UNIT WITH INSERTER AND TIE

TECHNICAL FIELD

The invention relates to hearing protectors and particularly to relatively flexible soft yieldable and pliable earplugs and means for inserting them into the auditory canal of the ear connected together as a compactable and wearable unit.

BACKGROUND ART

Known are various types of sound attenuating muffs and earplugs with insertion means that are an integral part of the earplug, a part of the earplug container or package or a separate easily lost or displaced loosely packaged part in the earplug container or box.

Also, known are various types of connecting and supporting means attached to a pair of muffs or earplugs.

However, the prior art earplugs to which the invention pertains are not as easily insertable due to their size, resiliency and flexibility of the material of which they must be made of to sealingly conform with the wall of the auditory canal. Additionally, the separately provided earplugs and insertion means are easily misplaced or lost.

The object of the instant invention is to provide an easily packagable, compactable and wearable earplug and earplug inserter unit or assembly in which the inserter and at least one or each of the earplugs or a pair of the earplugs are tied together to prevent separations and misplacement of one from the other.

DISCLOSURE OF THE INVENTION

A pair of earplugs each having a relatively flexible stem portion and adjacent spaced flanges of varying size made of relatively soft, yieldable, resilient material which readily conforms to sealingly engage the wall of the auditory canal of an ear. A flexible tie member extends between and is fixed at its opposite ends to the flexible stems of the earplugs. The tie member is threaded through a tubular earplug inserter slideably moveable thereon between and for insertably engaging the ear plugs.

In another embodiment at least one or each of the earplugs have a separate flexible tie member threaded through and retaining the earplug inserter thereon.

BEST MODE OF CARRYING OUT THE INVENTION

Figure 1:
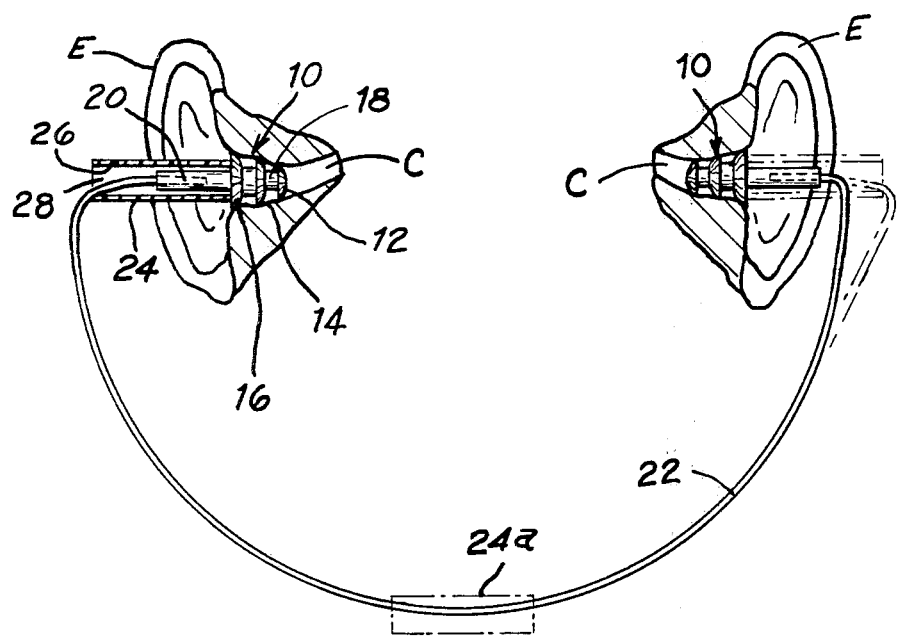
FIG. 1 is a view showing a pair of earplugs inserted into the auditory canals connected by a flexible tie cord and an earplug inserter, carried by the cord and movable between the earplugs, shown in a position for inserting an earplug and in its intermediate carrying position shown in phantom lines.

A pair of substantially identical earplugs 10 are shown in FIG. 1 inserted into the auditory canals C of the ears E. Each of the earplugs 10 has, adjacent one of its ends, a sound sealing portion insertable into the auditory canal of an ear for sealingly engaging the wall thereof. As shown the sealing portion situated at the inner end portion of the earplug has axially spaced flexible resilient flanges 12, 14 and 16 of progressively increasing diameter connected by and to a central portion or core 18 of relatively smaller diameter and short axial length. At its opposite outer end the earplug has a relatively long stem 20 adjoining and extending axially from the exterior and largest flange 16.

Means are provided for connecting the pair of earplugs together comprising a relatively long continuous flexible cord 22 fixed to and extending between the stems 20 of the earplugs 10. The flexible cord 22 can be mechanically or adhesively fixed to the earplugs and made of a variety of suitable materials such as plastic, metal, cotton, twine or string in the form of a continuous single solid strand or a strand made up of a plurality of braided or twisted filaments of man-made, plant or animal grown material.

Means for inserting each of the earplugs into the auditory canal is provided comprising an inserter 24 slideably mounted on and carried by flexible tie cord 22 for movement into and from engagement with each of the earplugs 10.

Preferably the earplug inserter 24 is a relatively short cylindrical open ended tubular or hollow member made of or cut to length from any suitable material such as plastic, metal, wood, ceramic, fiber, glass and paper tubes of greater rigidity, less flexibility and resiliency than the earplug material. The inserter comprises a cylindrical wall 26 extending between opposite substantially flat ends or end surfaces and about an internal chamber 28 of greater length and cross sectional size or area than the stem 20.

To insert an earplug 10 the inserter 24 is held between the fingers, and moved along the cord 22 and slipped over the stem 20 as shown in FIG. 1 until one end thereof engages the outer flange 16 whereafter the flanged sealing portion of the earplug is positively and more effectively inserted into sealing engagement with the surrounding wall of the auditory canal.

After insertion of the earplugs the inserter 24 is preferably moved along the cord to an intermediate carrying position 24a shown in phantom lines.

Figure 2:
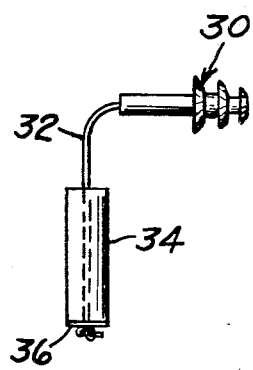
FIG. 2 shows another embodiment wherein at least one or each earplug is connected to a flexible cord on which an earplug inserter is movably retained.

Another embodiment of the invention shown in FIG. 2 comprises at least one earplug or each earplug 30 of a pair of earplugs substantially identical to the earplugs 10, only one of which has been shown, connected to one end of an individual or separate tie cord 32 which is relatively much shorter than the tie cord 22, and threaded through an earplug inserter 34 slideably mounted and retained thereon by suitable retainer or stop means at the opposite free end portion of the cord 22.

Preferably, retainer means comprises a washer or disc like member 36, fixed to the opposite end portion of cord 32. Alternatively, the washer or disc 36 may have a hole through which the flexible cord 32 passes and tied in a knot at the free end to maintain it and the inserter on the cord.

The earplug inserter 34 is substantially identical to inserter 24, but may be modified to have a single open end and an integrally formed end wall with a hole through which the cord 32 may pass and knotted or fixed thereto to retain the inserter therein.

The earplug 30 is inserted by manually moving the inserter 34 along the cord 32, and slipping it over the stem into engagement with the outer flange of the earplug 30 in the same fashion or described in connection with the insertion of the earplugs 10.

Thereafter the inserter 34 is preferably moved therefrom to a position at the end of the cord 32 and allowed to hang therewith from the ear until the earplug is removed therefrom.

In connection with means for retaining the insertion means on the tie cord or member it is to be understood that the earplug at one or both ends of the tie cord constitute at least a part of the retaining means.

Each of the earplugs, inserter and flexible tie cord assembly unit or disclosed hereinabove are relatively lightweight and are easily compacted or folded together and placed into the usual conventional carrying box or container not shown.

Although, specific examples of the invention have been described it is obvious that the many modifications thereof are possible. For example, the earplugs can be any one of a number of the conventionally and commercially available earplugs of various sizes, shapes and design or construction. The earplug 10 need not have a stem 20 since the tie cord 22 could be fixed to and extend from the center or core of the exterior flange 16 or an outer end of an earplug.

As many embodiments of the invention are possible it is to be understood that the embodiments disclosed hereinabove and shown in this accompanying drawing are for illustrative purposes only and that the invention includes all modifications, embodiments and equivalents falling within the scope of the appended claims.

What is claimed is:

1. An earplug unit comprising:
   at least one earplug adapted to be inserted into an auditory canal of an ear; a tie member having
   at least one of its opposite ends attached to an outer end of an earplug;
   insertion means carried by, retained on and movable along the tie member for engaging and inserting the earplug into the auditory canal; and means, attached to an opposite end of the tie member, for retaining the insertion means on the tie member.

2. An earplug unit according to claim 1 wherein the means for retaining the insertion means on the tie member comprises an earplug whereby the tie member is attached to and extends between a pair of earplugs retaining the insertion means between them on the tie member.

3. An earplug unit according to claim 1 wherein the tie member comprises:
   a flexible foldable cord passing through the insertion means.

4. An earplug unit according to claim 1 wherein the insertion means comprises:
   a tubular member through which the tie member passes having
   at least one end surface for engaging and inserting an earplug into the auditory canal.

5. An earplug unit according to claim 1 wherein the means for retaining the insertion means comprises:
   a knot tied at the opposite end of the tie member.

6. An earplug unit according to claim 1 wherein each earplug comprises:
   a sealing portion insertable into the auditory canal and situated adjacent an inner end of the earplug and a stem portion adjoining and extending from the sealing portion to an outer end of the earplug attached to the tie member.

7. An earplug unit according to claim 6 wherein the sealing portion comprises:
   a plurality of axially spaced flexible resilient sealing flanges including
   an inner flange of relatively small diameter adjacent the inner end of the earplug and an exterior flange of relatively larger diameter adjoining the stem portion over which the insertion means is slipped into engagement with the exterior flange for inserting the sealing portion into the auditory canal.

* * * * *